(12) United States Patent
Konoske et al.

(10) Patent No.: US 7,707,042 B1
(45) Date of Patent: Apr. 27, 2010

(54) COMPUTER IMPLEMENTED PROGRAM, SYSTEM AND METHOD FOR MEDICAL INVENTORY MANAGEMENT

(75) Inventors: Paula Konoske, San Diego, CA (US); Michael Galarneau, San Diego, CA (US); Gerald Pang, San Diego, CA (US); Tim Daly, Carlsbad, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 2956 days.

(21) Appl. No.: 10/209,954

(22) Filed: Aug. 1, 2002

Related U.S. Application Data

(60) Provisional application No. 60/346,667, filed on Jan. 8, 2002.

(51) Int. Cl.
| | |
|---|---|
| *G06Q 10/00* | (2006.01) |
| *G06Q 50/00* | (2006.01) |
| *G06Q 40/00* | (2006.01) |
| *G06F 19/00* | (2006.01) |
| *A61B 5/00* | (2006.01) |

(52) U.S. Cl. .................... 705/2; 705/3; 705/4
(58) Field of Classification Search ............ 705/2, 705/3, 4
See application file for complete search history.

(56) References Cited

U.S. PATENT DOCUMENTS

| | | | | |
|---|---|---|---|---|
| 4,156,539 A | * | 5/1979 | Davidson et al. ............ 283/105 |
| 4,221,404 A | * | 9/1980 | Shuffstall ..................... 283/115 |
| 4,236,332 A | * | 12/1980 | Domo .......................... 283/76 |
| 4,572,891 A | * | 2/1986 | Drexler ........................ 430/346 |
| 5,842,976 A | * | 12/1998 | Williamson .................. 600/300 |
| 5,848,593 A | * | 12/1998 | McGrady et al. ............ 128/897 |
| 5,912,818 A | * | 6/1999 | McGrady et al. ............ 700/232 |
| 5,971,593 A | * | 10/1999 | McGrady ..................... 700/233 |
| 5,993,046 A | * | 11/1999 | McGrady et al. ............ 700/231 |
| 6,085,493 A | * | 7/2000 | DeBusk et al. ................ 53/445 |
| 6,112,502 A | * | 9/2000 | Frederick et al. .............. 53/411 |
| 6,117,073 A | * | 9/2000 | Jones et al. .................. 600/300 |
| 6,163,737 A | * | 12/2000 | Fedor et al. .................. 700/236 |
| 6,454,709 B1 | * | 9/2002 | Kleinschmidt et al. ...... 600/300 |
| 6,594,634 B1 | * | 7/2003 | Hampton et al. ............... 705/3 |

\* cited by examiner

*Primary Examiner*—Gerald J. O'Connor
*Assistant Examiner*—Amber L Altschul
(74) *Attorney, Agent, or Firm*—Ryan J. Friedl; Kyle Eppele

(57) ABSTRACT

A system and method for estimating needed medical supplies based on a selected predefined operational scenario. A predefined operational scenario may be modified, a new operational scenario may be built, or a predefined operational scenario may be imported from an external source. A computer-readable program, system and method is provided for enabling a user to produce a query concerning relationships between patient conditions, tasks and medical supplies needed in specific locations. The production of a report or query is performed by referencing a database containing data pertaining to patient conditions, functional locations at which patients are to be treated (triage, operating room, etc.), equipment available in defined functional areas, tasks associated with treatment of defined patient conditions, medical supplies needed to carry out each defined task, and relationships therebetween, and determining needed medical supplies based on use data input and data contained in the database.

9 Claims, 8 Drawing Sheets

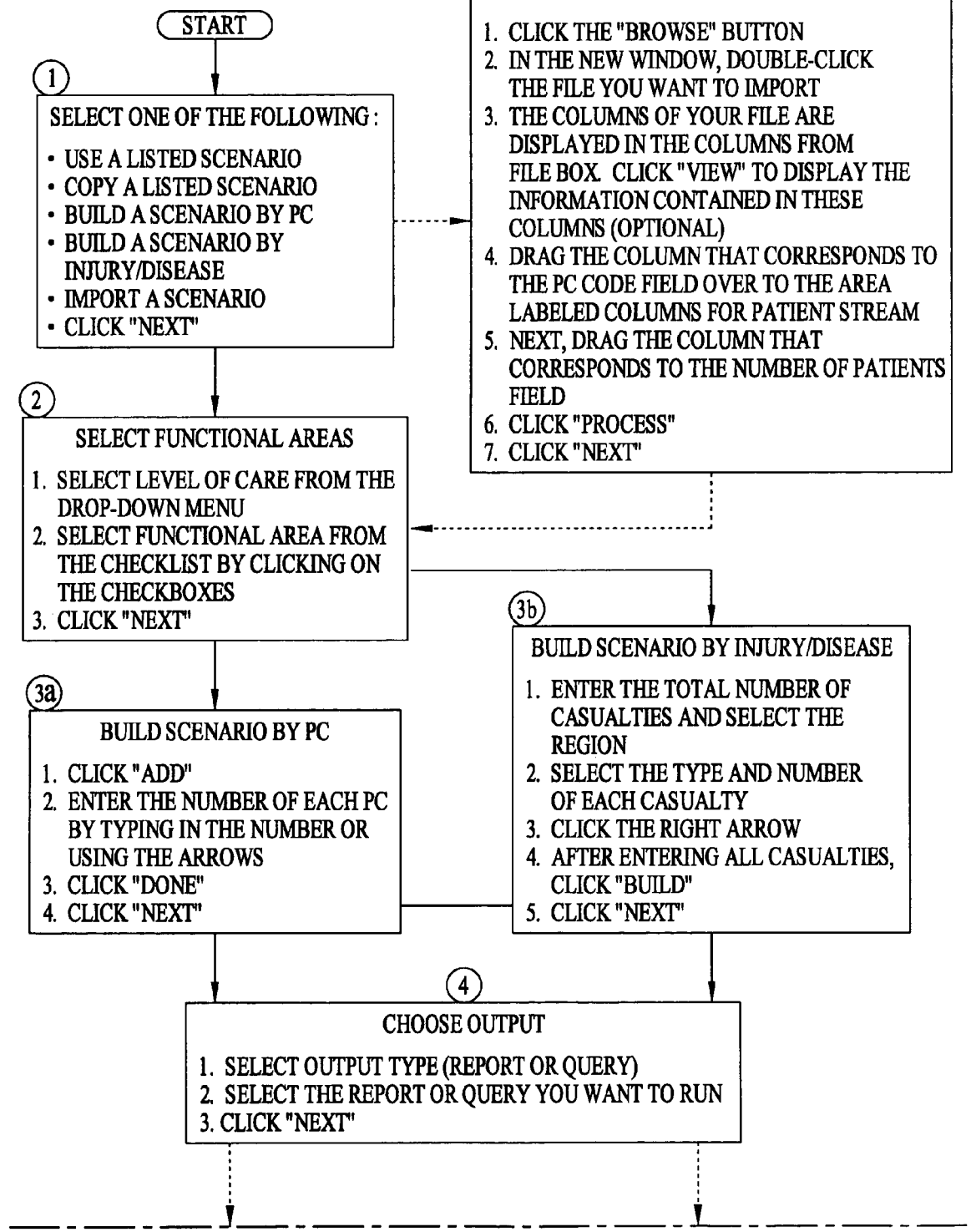

COMPUTER IMPLEMENTED PROGRAM, SYSTEM AND METHOD FOR MEDICAL INVENTORY MANAGEMENT

Two CD-ROM's are attached hereto and filed herewith in Appendix A herein, said CD-ROM's containing the computer program listing specified therein.

Under 35 USC 119(e), this application is entitled to and claims the benefit of the Jan. 8, 2002 filing date of the provisional application No. 60/346,667 entitled "Computer Implemented Program for Medical Inventory Management" filed by the same inventors named herein.

BACKGROUND OF THE INVENTION

1. Field of the Invention

The present invention provides a computer readable program, system and method for enabling a user to output a report of estimated needed medical supplies based on a selected operational scenario. In addition, a computer readable program, system and method is provided for enabling a user to produce a query concerning relationships between patient conditions, tasks and medical supplies needed in specific locations/situations. The source code for the Estimating Supplies Program version 1.1 computer program of the present invention has been submitted on CD-ROM as Appendix A herein. The material on the CD-ROM is hereby incorporated by reference.

2. Description of the Related Art

In conventional military operations, difficulty is frequently encountered in accurately estimating the medical supplies necessary to adequately supply military medical personnel in the field, especially in combat situations. Generally, Marine medical logistics planners determine which supplies are required by taking the expected number of casualties and comparing that to the notional total capability of each Authorized Medical Allowance List (AMAL) or Authorized Dental Allowance List (ADAL). This process has been found to be inaccurate and difficult, frequently causing over or under supply of vitally needed medical supplies. Oversupply causes unnecessary cost and burden, while undersupply causes inadequate care.

Thus, it is an object of the present inventors, representing the Naval Health Research Center (NHRC), to solve this problem by providing a computer readable program, system and method which enables a user to identify specific injuries and illnesses, and the corresponding system to determine the medical tasks required to treat patients with such specific injuries and illnesses (patient conditions), and supplies and equipment required to perform each task. To determine the amount of consumable supply requirements, a patient-generating model was used to project the frequency of specific injuries and illnesses likely to occur in a particular theater of operation.

It is a further object of the present invention to design a computer readable program, system and method capable of enabling a user thereof to query a database containing data concerning tasks, equipment and supplies needed in selected treatment locations (hereinafter "functional areas"), so as to enable the user to determine medical capabilities at selected sites and plan inventory therefor. These functional areas include triage, operating room, ward, etc.

SUMMARY OF THE INVENTION

To achieve the objects of the present invention described above, the present inventors developed the Estimating Supplies Program version 1.10 (hereinafter referred to as ESP), a computer readable program on a computer readable medium for use with a computer, a system, and a method used in a data processing system. This computer readable program, system and method enables a user to either create a user report describing medical supplies required to treat a patient stream based on data input by the user and/or data stored in a database accessible by the program, system and method, or to query said database upon request by the user, so as to obtain data concerning the relationships between patient conditions (PC's), tasks and supplies at specific functional areas.

Specifically, in a first embodiment, a computer program embodied on a computer readable medium for use with a computer for enabling a user to output a report of estimated needed medical supplies based on a selected scenario is provided, said computer program comprising:

computer readable code operable to enable interaction with a database comprising data concerning relationships between defined patient conditions, tasks required to treat each patient condition, the functional area and level of care for each task, and quantity and types of supplies needed for each task;

computer readable program code operable to enable a user to select a scenario;

computer readable program code operable to enable input of functional area and levels of care data into the operational scenario, so as to build a patient stream;

computer readable program code operable to reference said database so as to retrieve tasks required for each of said patient conditions;

computer readable program code operable to reference said database of operation scenarios so as to determine medical supplies needed to render care for each task;

computer readable program code operable to calculate total supplies consumed for each of said patient conditions; and computer readable program code operable to output a report to the user of necessary supplies and tasks each of said patient conditions from an operational scenario.

In a second embodiment of the present invention based on the first embodiment above, the computer program of the first embodiment above is provided, further comprising computer readable program code operable to enable input of data concerning casualty estimations by the user, so as to build an operational scenario, said operational scenarios comprising patient conditions and number of patients for each of said patient conditions.

In a third embodiment of the present invention based on the first embodiment above, the computer program further comprises computer readable program code operable to enable importation of a predefined operational scenario.

In a fourth embodiment of the present invention based on the third embodiment, the database of operational scenarios comprises one or more predefined scenarios.

In a fifth embodiment of the present invention according to the fourth embodiment above, the computer program further comprises computer readable program code operational to enable a user to modify a predefined scenario by altering predefined patient conditions and number of patients corresponding to each patient condition, so as to construct a scenario.

In a sixth embodiment of the present invention, a computer program embodied on a computer readable medium for use with a computer for enabling a user to produce a query concerning relationships between patient conditions, task and medical supplies needed to specific locations is provided, comprising:

computer readable code operable to enable construction of a database comprising data concerning relationships between defined patient conditions, tasks required to treat each patient condition, and quantity and types of supplies needed for each task;

a computer readable database concerning relationships between patient conditions, tasks pertaining to said patient conditions and medical supplies needed for said tasks;

computer readable program code operable to enable the user to input data concerning level of care;

computer readable program code operable to enable the user to input data concerning functional area;

computer readable program code operable to enable the user to select a type of query to be performed on said database;

computer readable program code operable to enable the user to create a type of query to be performed on said database; and computer readable program code operable to extract data from said database concerning patient conditions, tasks and supplies based on data input by the user concerning level of care and functional area.

In a seventh embodiment of the present invention, the computer readable program of the sixth embodiment above is provided, further comprising a database comprising data concerning relationships between defined patient conditions, tasks required to treat each patient condition, and quantity and types of supplies needed for each task.

In an eighth embodiment of the present invention, a system for estimating needed medical supplies for an operational scenario is provided, including a computer processor means for processing data, a storage means for storing a database of predefined operational scenarios on a storage medium, a data input means, and a data display means, comprising:

(a) a first means for enabling interaction with said database of predefined operational scenarios, said database comprising data concerning relationships between defined patient conditions, tasks required to treat each patient condition, functional area and level of care for each of said tasks, and quantity and types of supplies needed to perform each of said tasks;

(b) a second means for enabling a user to select a predefined operational scenario;

(c) a third means for enabling input of functional area and levels of care data into the operational scenario, so as to alter the treatment provided based on same;

(d) a fourth means operable to reference said database of operational scenarios so as to retrieve tasks required for each of said patient conditions;

(e) a fifth means operable to reference said database of operational scenarios so as to determine medical supplies needed to perform each of said tasks required for treating each of said patient conditions; and (f) A sixth means operable to output a report to the user of medical supplies and tasks associated necessary to treat each of said patient conditions defined in said operational scenario.

In a ninth embodiment of the present invention, a system according to the eighth embodiment above is provided, further comprising a seventh means operable to enable input of data by a user concerning casualty estimations, so as to build an operational scenario, said operational scenario comprising patient conditions and number of patients for each of said patient conditions.

In a tenth embodiment of the present invention, the system of the eighth embodiment above is provided, further comprising an eighth means operable to enable importation/selection by a user of a predefined operational scenario.

In an eleventh embodiment of the present invention, the system of the eighth embodiment above is provided, wherein said database of operational scenarios comprises one or more predefined scenarios.

In a twelfth embodiment of the present invention, the system of the eleventh embodiment above is provided, further comprising a ninth mean operable to enable a user to construct an operational scenario by selecting, and then modifying, a predefined scenario contained in said database, by altering predefined patient conditions and number of patients corresponding to each of said patient conditions.

In a thirteenth embodiment, a system is provided for enabling a user to produce a query concerning relationships between patient conditions, task and medical supplies needed in one or more specific locations, including a computer processor means for processing data, a storage means for storing a database of patient conditions, tasks and medical supplies needed in one or more specific locations on a storage medium, a data input means, and a data display means, comprising:

a first means operable to enable construction of a database of data concerning relationships between defined patient conditions, tasks required to treat each of said patient conditions, and quantity and types of medical supplies needed to perform each of said tasks;

a second means operable to enable the user to input data concerning level of care;

a third means operable to enable the user to input data concerning functional area;

a fourth means operable to enable the user to select a type of query to be performed on said database;

a fifth means operable to enable the user to create a type of query to be performed on said database; and a sixth means operable to extract data from said database concerning patient conditions, tasks and supplies based on data input by the user concerning level of care and functional area.

In a fourteenth embodiment of the present invention, the system of the thirteenth embodiment above is provided, further comprising a predefined database of data concerning relationships between defined patient conditions, tasks required to treat each patient condition, and quantity and types of supplies needed for each task.

In a fifteenth embodiment of the present invention, a method, in a data processing system, of estimating medical supplies needed for a selected operational scenario, is provided, the selected operational scenario comprising patient conditions and number of patients corresponding to each of said patient conditions, said method comprising the steps of:

(a) selecting an operational scenario by receiving input data from a user through a user interface;

(b) selecting level of care by receiving input data from a user through a user interface, said level of care defining medical capabilities available to a patient at a location corresponding to the selected operational scenario;

(c) selecting functional area by receiving input data from a user through a user interface;

(d) referencing a database stored on a storage medium containing data concerning operational scenarios, patient conditions, levels of care, functional areas, tasks and medical supplies necessary to perform each of said tasks, to determine tasks required for each patient condition associated with the operational scenario selected in (a);

(e) storing of said tasks determined in step (e), and storing of number of times each task is performed for each day of care required for each patient condition, in the storage medium;

(f) referencing said database to determine medical supplies needed to perform each of said tasks determined in step (d) and stored in step (e);

(g) calculating total medical supplies consumed for each patient condition in the selected operational scenario;

(h) outputting a user report comprising medical supplies and tasks needed for the selected operational scenario by displaying said report to the user through said user interface.

16. The method of claim 15, wherein the selected operational scenario is a predefined operational scenario stored in said database.

In a seventeenth embodiment of the present invention, the method of the sixteenth embodiment above is provided, wherein selection of the operational scenario of step (a) is performed by modifying a predefined operational scenario stored in said database, said method comprising the steps of:

(a)(1) importation/selection of a predefined operational scenario by a user;

(a)(2) modification of patient conditions defined by said predefined operational scenario by the user by receiving input data from a user through a user interface, so as to produce modified patient conditions; and (a)(3) modification of number of patients for each of said modified patient conditions by a user by receiving input data from a user through a user interface.

In an eighteenth embodiment of the present invention, the method of the fifteenth embodiment above is provided, wherein selection of the operational scenario of step (a) is performed by building a new operational scenario, said method comprising the steps of: (a)(1) selecting one or more patient conditions defined in said database;

(a)(2) selecting number of patients for each of said patient conditions;

(a)(3) building a new operational scenario comprising the patient conditions and number of patients selected in steps (a)(1) and (a)(2); and (a)(4) storing said new operational scenario as a predefined scenario in the database.

In a nineteenth embodiment of the present invention, the method of the fifteenth embodiment above is provided, wherein selection of the operational scenario in step (a) is performed by importation of an operational scenario by a user from an external source through a user interface.

BRIEF DESCRIPTION OF THE DRAWINGS & APPENDICES

Figure 1:
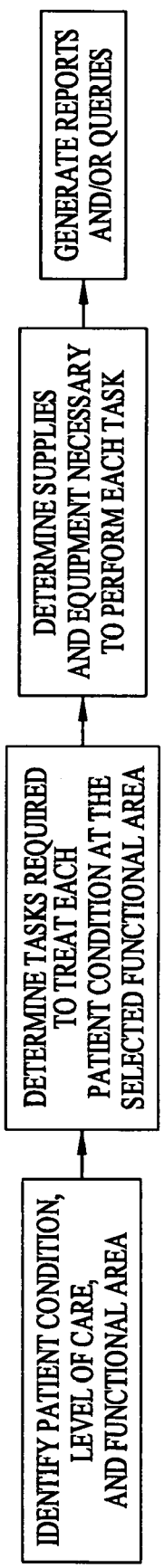
FIG. 1 is a flow chart diagram illustrating the general flow of data in ESP (the trade name of the computer readable program, system and method of the present invention) when running reports and/or queries.
Figure 2:
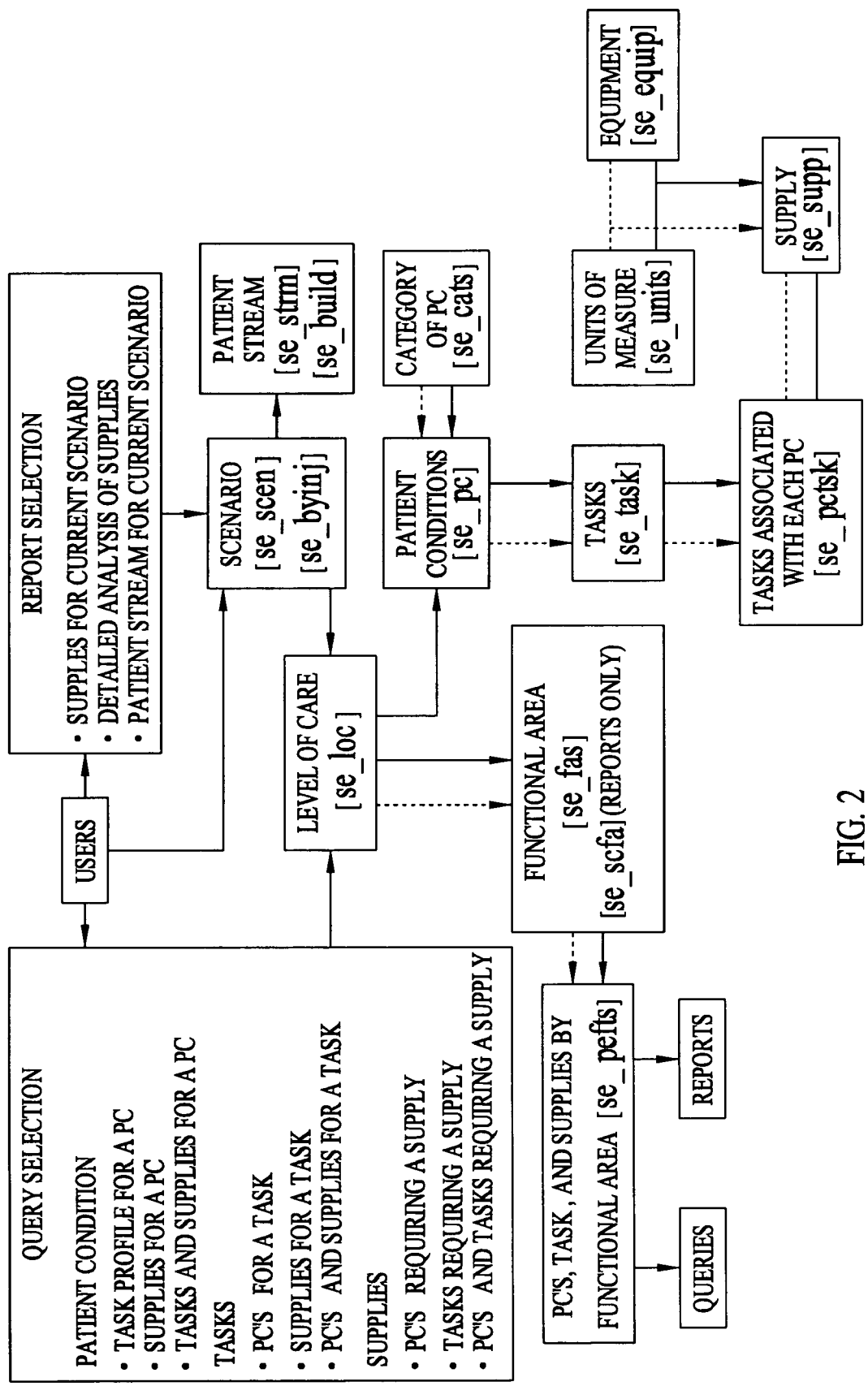
FIG. 2 is a flow chart diagram more specifically illustrating the data input steps/processes performed by users of the ESP computer readable program, system and method of the present invention to obtain reports and/or queries.
Figure 3:
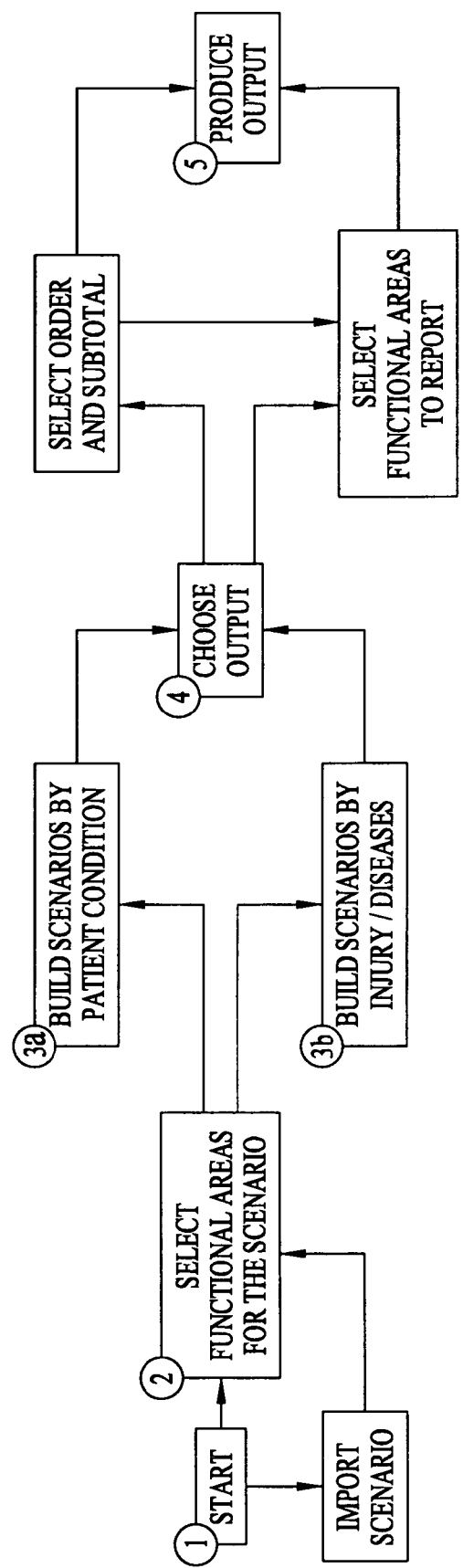
FIG. 3 is a program flow chart, illustrating steps to be taken by a user of the computer readable program, system and method of the present invention to produce a report or query.
Figure 4B:
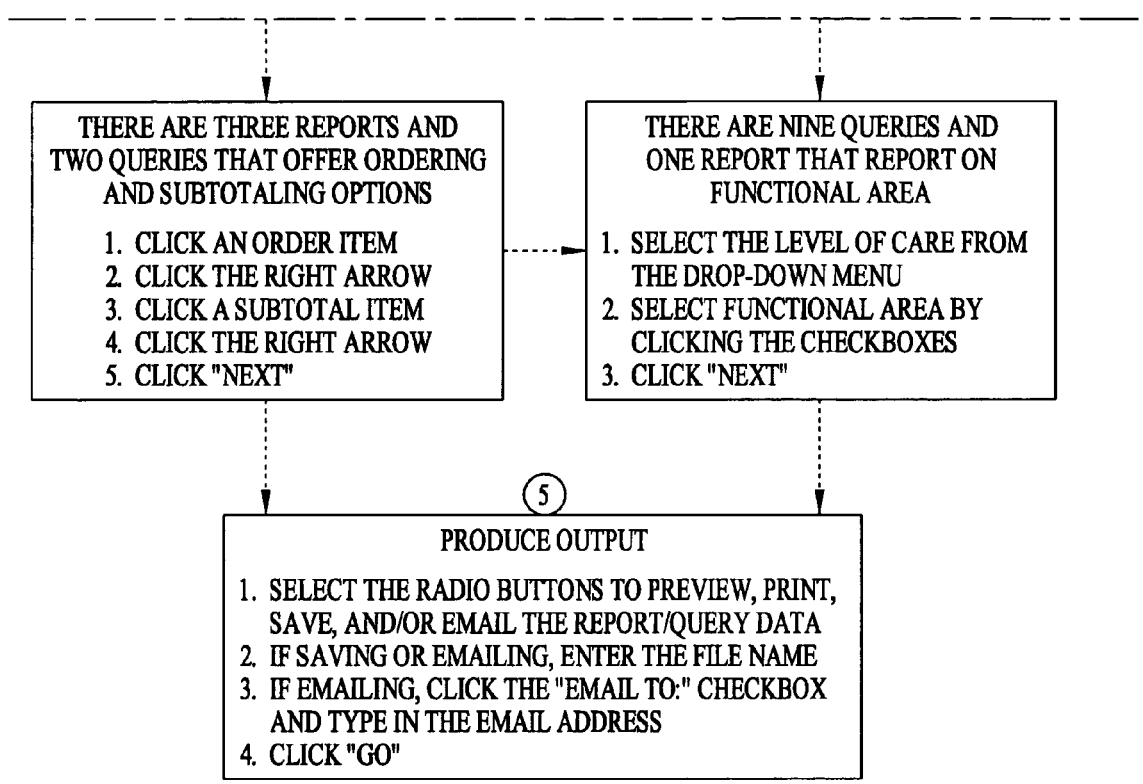
FIG. 4 is a step-by-step listing of instructions for use of the computer readable program, system and method of the present invention.
Figure 5:
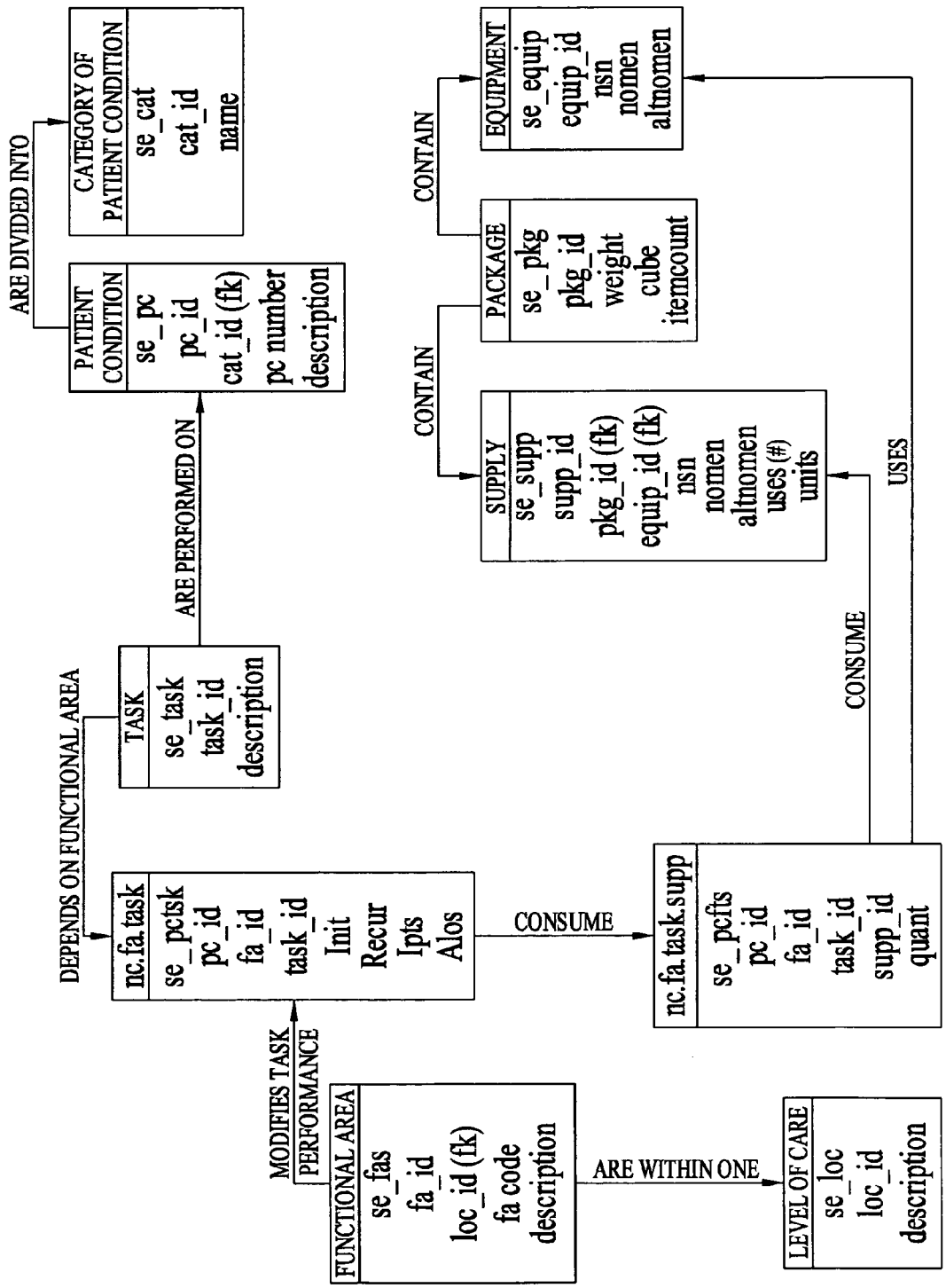
FIG. 5 is an entity relationship diagram for the computer readable program, system and method of the present invention.
Figure 6:
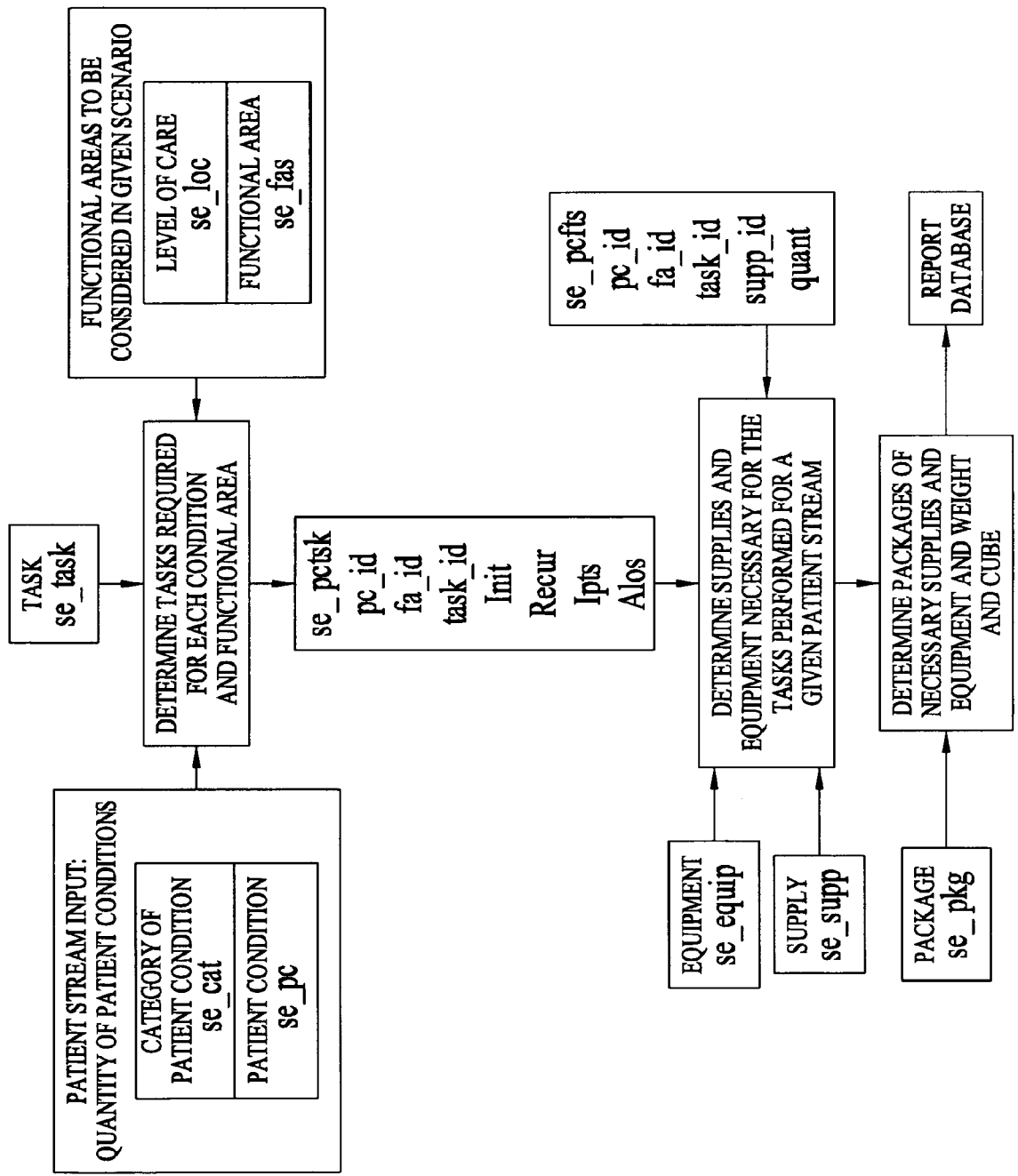
FIG. 6 is a data flow diagram of calculations performed by the computer readable program, system and method of the present invention.
Figure 7:
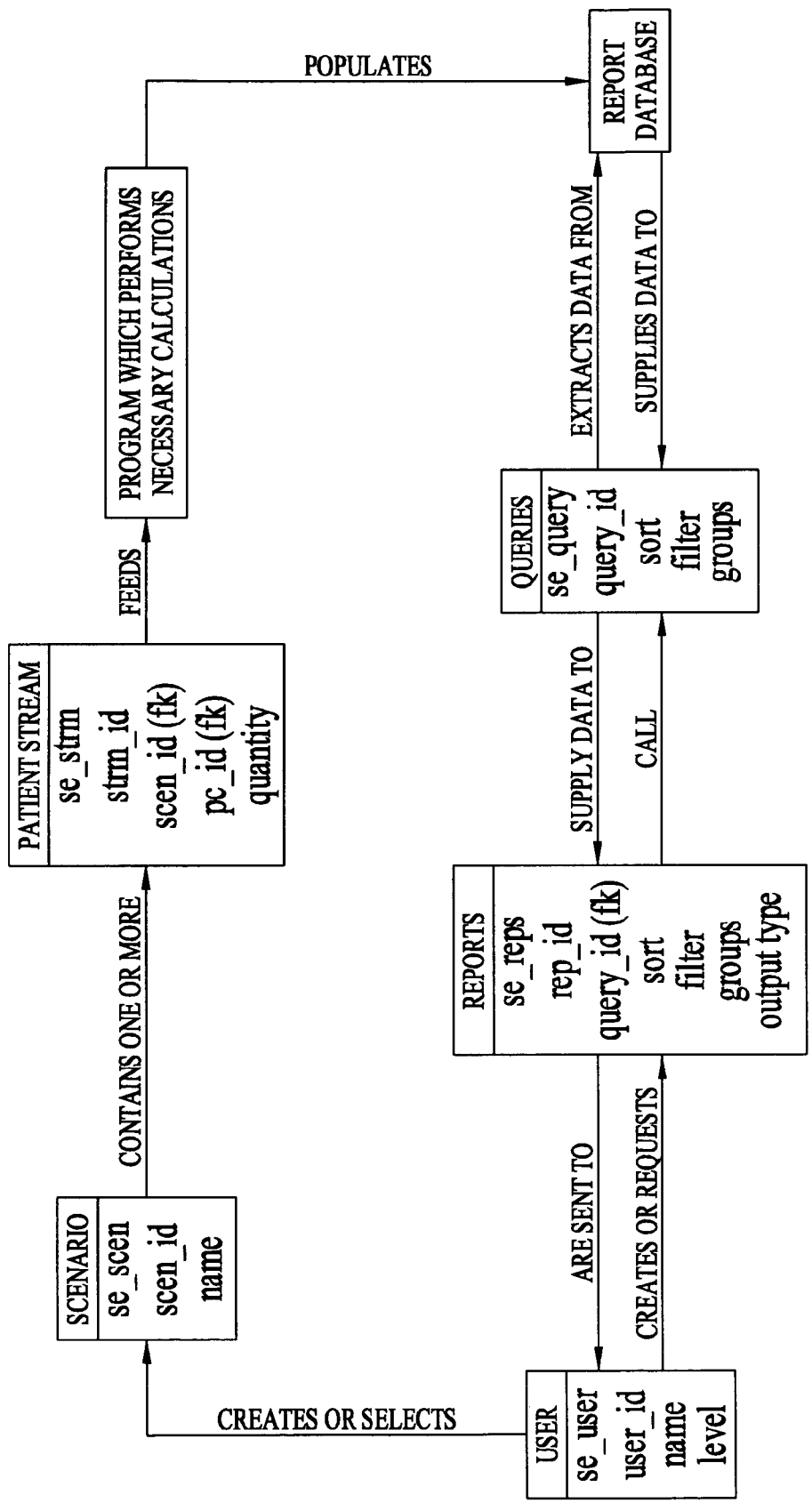
FIG. 7 is a data flow diagram of the user interface of the computer readable program, system and method of the present invention.

Appendix A contains 2 CD-ROM's, said CD-ROM's containing the source code of the computer readable program and system of the present invention.

Appendix B comprises the system documentation booklet for the computer readable program code, system and method of the present invention.

Appendix C comprises the user's guide for the computer readable program, system and method of the present invention.

DETAILED DESCRIPTION OF THE EMBODIMENTS

The inventors of the present invention endeavored to design, develop and utilize a systematic process to review military medical supply requirements, and a method and system of producing data in the form of user reports and/or queries to enable users of the computer program, system and method of the present invention to tailor the medical supplies needed specifically to the location, expected patient stream, etc. In order to achieve these objects, identification of medical tasks required to treat patients with specific illnesses (hereinafter referred to as patient conditions, PC's), and supplies and equipment needed for each task, was performed.

For example, to determine the amount of consumable supply requirements, a patient-generating model was used to project the frequency of specific injuries and illnesses likely to occur in a military theater of operation, i.e., the PC's and number of patients corresponding to each. An extensive database was created through such studies, which catalogues PC's, and the tasks and supplies required to treat each PC. This database is then accessed when using the computer program, system and method of the present invention, to obtain information necessary to calculate output data (user reports and queries) requested by a user of the program, system and method, i.e., to assist ESP users in efficiently planning medical resource requirements, to assist ESP system administrators at NHRC (Naval Health Research Center) with maintenance of the database, and to enable enhancement of program capability.

Based on these studies, and the implementation of the computer program, system and method of the present invention in determining the medical supplies needed in such theater, substantial reductions of up to 30% in the number of items, weight and cube (volume occupied by the items) may be achieved. This reduction reduces the logistical burden carried by military units in the field, and enhances far-forward clinical capability.

Hardware requirements for the operation of the computer program of the present invention are a digital PC in IBM format or 100% compatible PC with at least a 386 microprocessor, but preferably at least a Pentium microprocessor, a minimum of 16 MB of free RAM, but preferably at least 32 MB of free application RAM, and a minimum of 20 MB of free hard disk space.

Software requirements for operation of the computer program of the present invention are at least a Windows 95 or NT3 operating system, but preferably a Windows 98 or NT4 operating system, at least MS Office 97 or 2000, and at least an IE4 web browser, but preferably an IE5 web browser. Further, the computer program of the present invention uses SMTP email client to email results of queries and reports to users.

ESP (estimating supplies program) of the present invention allows the user to either:

(1) generate data concerning the supplies required to treat a patient stream in a specified scenario in the form of an ESP report; or (2) to query the database to learn about the relationship among PC's (patient conditions), tasks and supplies at specific functional areas in the form of an ESP query.

Production of a user report requires selection of a scenario, while a query does not require selection of a predefined or user-established scenario. To run (create) an ESP user report, the user must establish a patient stream by either selecting a defined scenario, copying and modifying a scenario, building a new scenario, or importing a scenario from an outside data source, such as an Excel spreadsheet. In each method, the user identifies (inputs through a user interface) a patient stream consisting of injuries and illnesses most likely to occur in deployments and conflicts (PC's), and selects the level of care and functional area to be used in the calculations performed by the computer program, system and method of the present invention. ESP uses these inputs to determine the tasks to be performed and the concomitant supplies to be consumed in order to render care. The user may output these program results in many formats (e.g., Word document, Excel spreadsheet, or printed report). The user may also email the results to a specified recipient. FIG. 1 herein illustrates the general flow of data in ESP when running reports and/or queries.

The ESP computer program, system and method of the present invention identifies the medical tasks required to treat patients with specific injuries and illnesses (PC's), accesses a database to estimate supplies and equipment based on a given patient stream distribution (defined by PC's and number of patients corresponding to each PC), and determines the supplies and equipment required by each task. To determine the amount of consumable supply requirements, a patient-generating model is used to project the frequency of specific injuries and illnesses likely to occur in the particular theater of operation.

The system of the present invention was developed using Microsoft Visual Studio 6.0. The tables, forms, libraries, reports, and queries were all designed using Visual FoxPro (VFP 6.0). Data is stored in VFP tables and retrieved by ESP using VFP queries and reports. The design philosophy of the present inventors was to build an application that could use output from other software applications, such as casualty estimating programs, in several formats, and provide data output in these formats. The input and output of the software of the present invention includes Excel spreadsheets, ASCII comma separated files and text files, dBase, FoxPro, Microsoft Word, and HTML tables.

In order to run ESP, the user must be able to choose a defined scenario, build a patient stream by entering a number of patients for each PC, or build a patient stream by identifying how many patients are exhibiting each injury or disease type. The user has the option of selecting a predefined scenario (e.g., Northeast Asia, Heavy Battle Intensity). The user may, alternatively, copy an existing scenario and modify it, import a patient stream from another data source (e.g., Excel spreadsheet or ASCII text file created by a casualty estimator), or build a new scenario by input of patient data, level of care data and functional location data.

If the user chooses to build a new scenario, s/he may either enter the number of patients exhibiting each PC or enter the total number of casualties by injury and disease type. The user must also enter level of care and functional area, having the option to report on a subset of the selected functional areas. Scenarios are saved upon creation, and users may then add, modify, or delete scenarios they create. Users may neither modify nor delete scenarios created by another user and stored as a predefined scenario.

The user must also select the level of care and functional areas where casualties receive treatment. The levels of care refer to the type of location a patient is to be treated in, and the medical capabilities such location has. Levels of care include First Responder, Battalion Aid Station, Forward Resuscitative Surgery (FRS)/Shock Trauma Platoon (STP), Surgical Company, Small Ships/Independent Duty Corpsman, Submarines, Landing Ship Dock (LSD's)/General Medical Officer (GMO), LHA's/LHD's and Aircraft Carriers. Functional areas refer to the type of medical facility the patient will be treated in. The functional areas include triage/SST, operating room, ward, x-ray, lab, battle dressing station, portable medical locker, first-aid boxes, emergency response kits, junior emergency response kits and dental.

The structure of the system is based on two levels of access. The first level user (level 1) is a program developer who has access to data maintenance functions. The second level user (level 0) is an end user of the computer program, system and method who does not have direct access to database tables. This structure was created to maintain database integrity. Furthermore, all users must enter a password to enter the system.

Where practical, the ESP program/system attempts to prevent invalid data entry upon input. For example, when a user fails to select a PC, but attempts to generate a query requiring at least one PC as a parameter, the program/system reminds the user to enter a PC. There are many calculations involved in determining the medical supplies necessary for a given patient stream. By storing the necessary information in tables, ESP queries the tables to get a result set.

The tables used in the processing of PCs, tasks, and supplies are maintained in a database, and may be updated to include new functional areas, revised treatments, new technology, or new injury or disease types. A mathematical algorithm is used to calculate the supply estimation necessary for a given patient stream for all of the PCs.

For all PCs, the following calculation is performed by the computer program, system and method of the present invention:

(number of patients*(Initial use*IPTS[1])*quantity)+
(number of patients*(Recur[2]* IPTS[1]*{ALOS[3]/24}−1)*quantity)

1) IPTS is the percentage of patients with a specific PC who require a specific task.

2) Recur is the number of times the task is repeated after the first day of treatment.

3) ALOS is the Average Length of Stay measured in hours.

More specifically, with regards to the processing functions of the computer program, system and method of the present invention, when the user [se_user] starts ESP, s/he must decide whether to work with an operational scenario or query the database. If working with an operational scenario, the user must either select a listed operational scenario, select and modify a listed operational scenario, import an existing operational scenario from another file, or build a new operational scenario [se_scen]. Regardless of the selected option, the user must input level of care and functional area, and typically does so before actually building the patient stream.

[se_loc] is a table that lists the available level of care (e.g., First Responder, BAS, SC), while table [se-fas] lists the available functional areas (e.g., Triage, Operating Room, Ward). Once the user chooses the desired data inputs, ESP stores this input data in the [se_scfa] table. When the user chooses to import an operational scenario, the data is copied to a .dbf file with the same name as the source file. The [se_scen] and [se_strm] tables are populated directly from the .dbf file.

In the instance that a user builds or modifies an operational scenario by input of PC data by a user through a user interface, ESP references both the [se_pc] table that lists all available PC's by code number (e.g., PC 001 is a cerebral concussion closed with/without nondepressed linear skull fracture severe-loss of consciousness from 2 to 12 hours), and the [se_cats] table that lists PC's by category. The PC's selected by the user are stored in the [se_strm] table. This table also contains the integral number of patients and the probability of these patients exhibiting the selected PC.

When a user builds an operational scenario by input of injury and disease-type data, ESP references the [se_byinj] table. This table stores the probabilities of casualties exhibiting injury and disease conditions by geographical location, how the condition occurred (e.g., wounded in action [WIA], non-battle injury (NBI), disease), type of condition (e.g., burn, inhalation), and physical location (e.g., arm, head). The user selects casualties by these same criteria and this data is stored in the [se_build] table. The available injury/disease types are assigned a PC code. A probability is used to simulate a fractional (non-integer) number of patients between zero and one (this situation may also occur when importing data from an external source with non-integer patients). Then, ESP divides the number of patients by the PC's assigned to that injury or disease type. However, the number of patients may not be evenly divisible by these PCs. If there is more than one patient, the system rounds off to the nearest integer. To avoid eliminating PC's or overestimating required supplies, the system converts patient numbers with the value of less than one to a probability, and replaces the number of patients with one. As a result, the total number of patients may slightly exceed the projected total of patients.

At this point, the user has completed building the patient stream. To generate a list of tasks associated with each PC in each functional area, ESP cross references the [se_strm] table with the [se_task] table, which lists all existing tasks required for the treatment of each PC. The result of this cross-reference is stored in [se_pctsk] in the form of a list of tasks required to treat the patient stream. [se_pctsk] also contains the number of times the task is performed on Day 1, the number of times the task is repeated on Day 2, and every subsequent day thereafter, the percentage of times the task is performed for the specific PCs, the average length of stay of a patient, and the treatment time.

Each task has a list of supplies required for performance at each functional area. The [se_supp] table is a list of supplies that includes nomenclature, National Stock Number (NSN), weight, cube, cost and type (ECD: equipment, consumable, durable). Units of measure are stored in [se_units] table and equipment items are listed in the [se_equip] table. The quantities of each supply required for each task performed at each functional area are extracted from the [se_pcfts] table.

The user may now run (output) a user report pertaining to the selected operational scenario (ESP still allows the user to select a query at this point, if desired). The computer program, system and method of the present invention offer the user the choice of several different types of user reports, including ordering and subtotaling features, and also allow the user to report on a subset of the selected functional areas. Lastly, the user identifies the desired format of the output (e.g., Word, Excel), as well as how to receive this output (e.g., save, print, email).

With regards to the data output functions of the present invention, ESP offers two types of output: user reports and queries. A user report includes data that is relevant to a defined patient stream. A query contains information from the ESP database that is not dependent on a patient stream. Output is formatted landscape or portrait, depending on which orientation best suits the data displayed. Orientation is determined by the selection of the report/query and cannot be altered by level 0 users.

The data entered by the users, and the data used to calculate results, are stored in Visual FoxPro tables contained in a database. The stored procedures in this database include a function to assign new unique keys when records are added to tables. Most tables also have a unique key field that contains a unique value generated by ESP to help maintain data integrity.

Use of the computer program, system and method of the present invention provides a new method of reducing the logistical burden carried by military units in the field, by reducing excess medical inventory capacity, by enabling the logistician or planner to more accurately determine the supplies needed to treat a flow of casualties. This is achieved by looking at the patient distribution constituting a patient stream, the respective treatment to be provided to such a patient stream, and the supplies required to perform those treatments.

This is achieved in part by the development of a patient generating model, which projects the frequency of specific injuries and illnesses likely to occur in a given theater, and the necessary tasks and supplies that will be needed to treat such illnesses and injuries. One of the main products of the computer program, system and method of the present invention is a user report, providing the user with detailed data concerning weight of the necessary medical supplies, cube (area occupied by said supplies), and cost of said supplies, which enables the user to accurately determine cost and ability to transport a given supply of medical goods. Implementation of the computer readable program of the present invention has been found to reduce the amount of medical items by as much as 30%, with concomitant savings in weight, cube and cost.

GLOSSARY OF TERMS USED HEREIN

Database—A collection of Tables and Views with associated stored procedures.

Entity—A person, thing, or abstract business concept. In database design, it is the thing that the table represents.

Field—A single column of information in a table.

Foreign Key A Primary Key from one table that is in another table to establish a relationship between the two tables.

Patient Condition—An injury or disease that corresponds to a patient condition code number and is exhibited by a patient.

Patient Stream—A list of patient conditions and the associated number of patients exhibiting that condition.

Primary Key—A unique identifying value in a record of a table.

Record—A single row of information in a table.

Scenario—A situation that results in a patient stream. Also, often used as a synonym of patient stream.

Stored Procedure—Code within a database used to maintain tables, assign key values.

Supply—A piece of equipment, durable item, or consumable item that is used in the treatment of patients.

Table—Information about a particular entity stored in a series of records with the same fields.

Task—A medical procedure performed on a patient.

View—The updateable result of a query. Several views are stored in the database. A parameterized view requires parameters that are used in running the query to produce the result. An example of a parameterized view is lv-addpcs, which accepts the current scenario and the current category as parameters and returns the set of patient conditions in the current category that are not included in the current scenario. This view is suitable for selecting patient conditions to add to the patient stream.

What is claimed is:

1. A computer program embodied on a computer readable medium for use with a computer for enabling a user to output a user report of estimated needed medical supplies based on a selected operational scenario, said computer program comprising:

computer readable code operable to enable interaction with a database of operational scenarios comprising data concerning relationships between defined patient conditions, tasks required to treat each patient condition, functional area and level of care for each of said tasks, and quantity and types of supplies needed to perform each of said tasks, wherein said database of operational scenarios comprises one or more predefined operational scenarios;

computer readable program code operable to enable a user to select an operational scenario from said database of operational scenarios;

computer readable program code operable to enable input of functional area and levels of care data into the selected operational scenario, so as to build a patient stream;

computer readable program code operable to reference said database so as to retrieve tasks required for each of said defined patient conditions;

computer readable program code operable to reference said database of operational scenarios so as to determine medical supplies needed to perform each of said tasks;

computer readable program code operable to calculate total supplies consumed for each of said defined patient conditions, said calculation based upon a projection of the frequency of specific injuries and illnesses likely to occur given the selected operational scenario; and computer readable program code operable to output a report to the user of estimated necessary medical supplies and tasks associated with each of said defined patient conditions from a selected operational scenario.

2. The computer program of claim 1, further comprising computer readable program code operable to enable input of data by a user concerning casualty estimations, so as to build an operational scenario, said operational scenarios comprising patient conditions and number of patients for each of said patient conditions.

3. The computer program of claim 1, further comprising computer readable program code operable to enable importation of a predefined operational scenario.

4. The computer program of claim 1, further comprising computer readable program code operational to enable a user to modify a predefined operational scenario by altering predefined patient conditions and number of patients corresponding to each patient condition, so as to construct a scenario.

5. A method, in a data processing system, of estimating medical supplies needed for a selected operational scenario, said method comprising the steps of:

(a) selecting an operational scenario by receiving input data from a user through a user interface, the selected operational scenario comprising patient conditions and number of patients corresponding to each of said patient conditions;

(b) selecting a level of care by receiving input data from a user through a user interface, said level of care defining medical capabilities available to a patient at a location corresponding to the selected operational scenario;

(c) selecting a functional area by receiving input data from a user through a user interface;

(d) referencing a database stored on a storage medium containing data concerning one or more predefined operational scenarios, patient conditions, levels of care, functional areas, tasks and medical supplies necessary to perform each of said tasks, to determine tasks required for each patient condition associated with the operational scenario selected in (a);

(e) storing of said tasks determined in step (e), and storing of number of times each task is performed for each day of care required for each patient condition, in the storage medium;

(f) referencing said database to determine medical supplies needed to perform each of said tasks determined in step (d) and stored in step (e);

(g) calculating total medical supplies consumed for each patient condition in the selected operational scenario, said calculation based upon a projection of the frequency of specific injuries and illnesses likely to occur given the selected operational scenario; and (h) outputting a user report comprising an estimate of medical supplies needed for the selected operational scenario by displaying said report to the user through said user interface.

6. The method of claim 5, wherein the selected operational scenario is a predefined operational scenario stored in said database.

7. The method of claim 5, wherein selection of the operational scenario of step (a) is performed by modifying a predefined operational scenario stored in said database, said method comprising the steps of:

(a)(1) importation/selection of a predefined operational scenario by a user;

(a)(2) modification of patient conditions defined by said predefined operational scenario by the user by receiving input data from a user through a user interface, so as to produce modified patient conditions; and (a)(3) modification of number of patients for each of said modified patient conditions by a user by receiving input data from a user through a user interface.

8. The method of claim 5, wherein selection of the operational scenario of step (a) is performed by building a new operational scenario, said method comprising the steps of:

(a)(1) selecting one or more patient conditions defined in said database;

(a)(2) selecting number of patients for each of said patient conditions;

(a)(3) building a new operational scenario comprising the patient conditions and number of patients selected in steps (a)(1) and (a)(2); and (a)(4) storing said new operational scenario as a predefined scenario in the database.

9. The method of claim 5, wherein selection of the operational scenario in step (a) is performed by importation of an operational scenario by a user from an external source through a user interface.

* * * * *